(12) United States Patent
Persson

(10) Patent No.: US 10,384,026 B2
(45) Date of Patent: Aug. 20, 2019

(54) TRACHEOSTOMA DEVICE HOLDER

(71) Applicant: Atos Medical AB, Horby (SE)

(72) Inventor: Jan-Ove Persson, Hoor (SE)

(73) Assignee: Atos Medical AB (SE)

( * ) Notice: Subject to any disclaimer, the term of this patent is extended or adjusted under 35 U.S.C. 154(b) by 731 days.

(21) Appl. No.: 14/651,139

(22) PCT Filed: Nov. 22, 2013

(86) PCT No.: PCT/EP2013/074478
§ 371 (c)(1),
(2) Date: Jun. 10, 2015

(87) PCT Pub. No.: WO2014/090549
PCT Pub. Date: Jun. 19, 2014

(65) Prior Publication Data
US 2015/0306327 A1 Oct. 29, 2015

(30) Foreign Application Priority Data

Dec. 11, 2012 (SE) ...................................... 1251404

(51) Int. Cl.
*A61M 16/04* (2006.01)
*A61F 13/12* (2006.01)
(Continued)

(52) U.S. Cl.
CPC ...... *A61M 16/0465* (2013.01); *A61M 16/047* (2013.01); *A61M 16/0497* (2013.01);
(Continued)

(58) Field of Classification Search
CPC .. A61M 16/00; A61M 16/04; A61M 16/0465; A61M 16/0468; A61M 16/047;
(Continued)

(56) References Cited

U.S. PATENT DOCUMENTS 3,952,335 A    4/1976   Sorce et al.
5,088,483 A *   2/1992   Heinecke .............. A61F 13/023
                                                                                 128/849
(Continued)

FOREIGN PATENT DOCUMENTS

CN           1662273 A     8/2005
CN      102256652 A    11/2011
(Continued)

OTHER PUBLICATIONS

Machine Translation of WO 2012/055389 A1.*
(Continued)

*Primary Examiner* — Colin W Stuart
(74) *Attorney, Agent, or Firm* — Fishman Stewart PLLC

(57) ABSTRACT

A tracheostoma device holder for holding a tracheostoma device superimposed of a tracheostoma of a person is provided. The tracheostoma device holder comprises a rigid plate for attachment over a tracheostoma via a proximal side thereof, the plate being provided with a through hole, and a tubular tracheostoma device fitting, arranged circumferentially of the through hole, the tubular tracheostoma device fitting extending distally from a distal side of the plate. The plate is manufactured in a thermoplastic material, with a melting/softening temperature allowing for molding according to the local anatomic shape of the person through direct contact between the plate and the skin of the person. A method for adaptation of such tracheostoma holding device is also provided.

15 Claims, 2 Drawing Sheets

(51) Int. Cl.
*A61M 16/10* (2006.01)
*A61F 13/00* (2006.01)

(52) U.S. Cl.
CPC ... *A61F 13/128* (2013.01); *A61F 2013/00412* (2013.01); *A61F 2013/00421* (2013.01); *A61M 16/0468* (2013.01); *A61M 16/1045* (2013.01); *A61M 2205/02* (2013.01); *A61M 2205/36* (2013.01); *A61M 2205/583* (2013.01); *A61M 2207/10* (2013.01)

(58) Field of Classification Search
CPC .......... A61M 16/0472; A61M 16/0497; A61M 2205/02; A61M 2207/10; A61M 2207/00; A61F 13/128; A61F 2013/00412; A61F 2013/00421
USPC ..... 128/862, 200.26, 207.14, 207.15, 207.29
See application file for complete search history.

(56) References Cited

U.S. PATENT DOCUMENTS

| | | | |
|---|---|---|---|
| 5,702,754 | A | 12/1997 | Zhong |
| 6,422,235 | B1* | 7/2002 | Persson ............. A61M 16/0468 128/200.26 |
| 6,830,565 | B2* | 12/2004 | Cisko, Jr. ................ A61F 5/443 604/336 |
| 7,025,784 | B1* | 4/2006 | Blom ....................... A61F 2/20 623/14.11 |
| 9,233,220 | B2 | 1/2016 | Persson |
| 2003/0029456 | A1* | 2/2003 | Lambert ........... A61M 16/0468 128/207.15 |
| 2004/0079374 | A1 | 4/2004 | Thornton |
| 2008/0072911 | A1* | 3/2008 | Flagler ............. A61M 16/0434 128/207.14 |
| 2011/0184327 | A1* | 7/2011 | Cameron ................ A61F 13/12 602/43 |
| 2011/0247629 | A1 | 10/2011 | Persson |
| 2012/0055485 | A1 | 3/2012 | Anthony |
| 2013/0192603 | A1* | 8/2013 | Leibitzki .......... A61M 16/0468 128/205.29 |
| 2013/0213404 | A1 | 8/2013 | Leibitzki et al. |
| 2014/0326247 | A1* | 11/2014 | Dirven .............. A61M 16/0468 128/207.16 |

FOREIGN PATENT DOCUMENTS

| | | | | |
|---|---|---|---|---|
| CN | 103906544 | A | 7/2014 | |
| DE | 202004007566 | U1 | 8/2004 | |
| DE | 202005012609 | U1 | 11/2005 | |
| DE | 102010049895 | A1 | 5/2012 | |
| EP | 0078685 | A1 | 5/1983 | |
| JP | H08-317970 | A | 12/1996 | |
| JP | 2005-529706 | A | 10/2005 | |
| JP | 2012-512677 | A | 6/2012 | |
| WO | WO-2004/000401 | A1 | 12/2003 | |
| WO | WO-2010/070087 | A2 | 6/2010 | |
| WO | WO-2010/0125074 | A1 | 11/2010 | |
| WO | WO 2012055389 | A1 * | 5/2012 | ........ A61M 16/0468 |
| WO | WO-2012/163994 | A1 | 12/2012 | |
| WO | WO-2013/032334 | A1 | 3/2013 | |

OTHER PUBLICATIONS

English Translation of Chinese Office Action for Application No. 201380062594.2.
Bibliographic Data Sheet indicating "No Abstract Available for DE202010014892-U1".
English Abstract for DE-202004007566-U1.
English Abstract for DE-202005012609-U1.
English Abstract for CN-103906544-A.
English Translation of Chinese Office Action for Application No. 201380062594.2, dated Mar. 3, 2017.
English Translation of Japanese Office Action for Application No. 2015-545733, dated Jun. 6, 2017.
English Abstract for JP-H08-317970-A.
Bibliographic Data Sheet indicating "No Abstract Available for JP-2005-529706-A", however WO-2004/000401-A1 is the English equivalent of JP-2005-529706-A.
Notice of Reasons for Rejection dated Mar. 5, 2109 related to corresponding Japanese Patent Application No. 2018-090764.

* cited by examiner

TRACHEOSTOMA DEVICE HOLDER

CROSS-REFERENCED TO RELATED APPLICATIONS

This application claims priority to International Patent Application PCT/EP2013/074478 filed Nov. 22, 2013 and Swedish Patent Application No. 1251404-8 filed Dec. 11, 2012, the contents of which are hereby incorporated by reference in their entirety.

TECHNICAL FIELD

The present invention pertains in general to a trachestoma device holder. More particularly, the present invention pertains to a trachestoma device holder, comprising a plate for attachment over a tracheostoma via the proximal side of the plate, said plate being provided with a through hole having a tubular tracheostoma device fitting extending distally from the plate circumferentially of said through hole. Additionally, the present invention pertains to a method for adapting such a trachestoma device holder to its intended user.

BACKGROUND

A tracheostomy is a surgical procedure in which an opening is formed through the anterior surface of the neck into the trachea. The opening is referred to as a tracheostoma. A tracheostomy tube can be provided to extend between the tracheostoma and the trachea. A tracheostomy is performed for example when there is a malfunction, such as a result from injury or disorder, in respect of the nervous system or the respiratory passages, which malfunction results in an incapacity to obtain enough air. An inferior lung capacity or need of respiratory treatment may also result in a tracheostomy.

A laryngectomy is a surgical procedure, used for example to treat a carcinoma, which involves removal of the larynx or voice box and the creation of a tracheostoma. A consequence of the procedure is that the trachea is no longer connected to the pharynx but is diverted to the tracheostoma. After this procedure, normal nasal function is not possible. In a subject whose breathing functions normally, the nose and the mucous membrane lining of the nasal cavity perform important functions in conditioning inhaled air. The convoluted passages and rich blood supply serve to increase both the temperature and humidity of the inhaled air to minimise the differential in these parameters with those of the surface of the lungs. Normally some heat and moisture is also captured from exhaled air prior to its release to the atmosphere. The mucous lining of the nasal passages also serves to remove particulate matter, such as fine dust particles, pollutants and microorganisms, from the inhaled air, and the action of cilia transports mucous and any particles away from the lungs.

When a person has received a laryngectomy, in effect all inhaled air enters the lungs via the tracheostoma, and the nose is effectively not involved in the inhalation process. Exhaled air may pass through the tracheostoma or, if a voice prosthesis has been fitted, the stoma can be occluded so that the exhaled air is diverted through the voice prosthesis into the pharynx and the mouth, enabling the person to speak. It is desirable that the flow of the exhaled air be controlled by means of a tracheostoma valve. In these situations, the valve can be arranged to remain open during breathing but can be closed to divert the airflow, through a small additional increase in exhaled air flow.

In this respect tracheostoma devices, such as filter devices, HME, breathing protectors, and speech valves, have been developed to enable moisturizing of inhaled air, removal of small particles and bacteriological substances in said inhaled air, and providing the person with the ability to speak by closing the air passage through the trachestoma by manual operation.

These tracheostoma devices are held in place by a tracheostoma device holder, arranged above the tracheostoma of the person. The tracheostoma device holder is normally attached to the skin of the person by a plaster, having an adhesive surface on the side of the plaster intended to be directed towards the person in use. Either, the tracheostoma device holder is welded to the plaster, or the tracheostoma device holder is arranged on an adhesive surface on the side of the plaster intended to be directed outwards from the person in use. On the skin adhesive surface a covering sheet may be applied, which is removed just before application of the tracheostoma device holder. The covering sheet facilitates transportation, and maintains skin adhesive ability of the skin adhesive surface. A plaster of this kind is disclosed in EP 0 078 685 A1.

It is however a problem associated with the application of the tracheostoma device holder after the removal of the covering sheet, since the throat of the person receiving the tracheostoma device holder by no means is planar. It is difficult to adhere the tracheostoma device holder in the pit in between the sternocleidomastoid muscles, at persons with sunken stomas, i.e. stomas that somewhat has sunken into the throat of the person, since the adhesive surface of the tracheostoma device holder inevitably will adhere to the walls of the pit before reaching the bottom of the pit with the central portion of the system. Sunken stomas are very frequent in the group of persons not having the two vertical sternocleidomastoid muscles on the neck cut during laryngectomy. As a result, it is very common that the tracheostoma device holder flip over, since the bad connection between adhesives and skin and the axial displacement of the speech pressure resulting in loosening of the tracheostoma device holder and need of unduly high speech pressure.

Furthermore, in many hospitals the surgical steps during laryngectomy are adapted for creating stomas of substantially planar natures, to comply with the tracheostoma device holder system presently on the market. This adaptation includes the cutting of the two vertical sternocleidomastoid muscles on the neck.

Hence, an improved tracheostoma device holder would be advantageous, and in particular a tracheostoma device holder allowing for convenient application of the tracheostoma device holder with improved positioning ability, while simultaneously decreasing the risk of loosening of skin adhesion close to the tracheostoma, also in persons with sunken tracheostomas, thus keeping speech pressure at a convenient level, as well as making up for irregularities in skin shape adjacent the stoma.

SUMMARY

Accordingly, the present invention preferably seeks to mitigate, alleviate or eliminate one or more of the above-identified deficiencies in the art and disadvantages singly or in any combination and solves at least the above mentioned problems by providing a trachestoma device holder for holding a tracheostoma device superimposed of a tracheostoma of a person, said tracheostoma device holder comprising: a rigid plate for attachment over a tracheostoma via a proximal side thereof, said plate being provided with a through hole; a tubular trachestoma device fitting, arranged circumferentially of the through hole, said tubular trachestoma device fitting extending distally from a distal side of the plate; wherein the plate is manufactured in a thermoplastic material, with a melting/softening temperature allowing for molding according to the local anatomic shape of the person through direct contact between the plate and the skin of the person.

A method for adaptation of such tracheostoma holding device is also provided for the same reasons.

Advantageous features of the invention are defined in the dependent claims.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DETAILED DESCRIPTION

The following description focuses on an embodiment of the present invention applicable to a tracheostoma device holder, for holding a trachestoma device 100, such as a tracheostoma valve, over the stoma of a person. A tracheostoma device may in this context be a HME, speech valve, etc.

Figure 1:
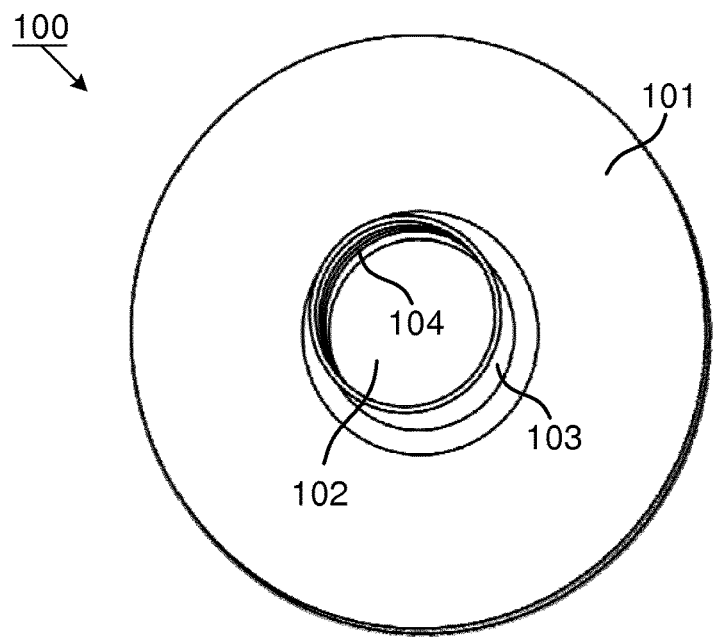
FIG. 1 is a perspective view of a tracheostoma device holder according to an embodiment of the present invention, in a pre-adapted form.

According to a first embodiment, disclosed in a perspective view in FIG. 1, the tracheostoma device holder 100 comprises a rigid plate 101 for attachment over a trachestoma via the proximal side of the plate 101. The plate 101 is provided with a through hole 102. Circumferentially of the through hole 102 a tubular trachestoma device fitting 103, such as a cylindrical sleeve, is provided. The trachestoma device fitting 103 extends distally from the plate 101 circumferentially of said through hole 102. The trachestoma device fitting 103 is made of a flexible and resilient material, such as a soft polyethylene, a polyethylene copolymer, a rubber, silicone, or mixtures thereof. In such configuration, the plate 101 will extend laterally as a flange from the tubular trachestoma device fitting 103, in relation to a central axis of the through hole 102. Similarly, the tubular tracheostoma device fitting 103 extends axially and distally from the plate 101, in accordance with above.

The trachestoma device fitting 103 comprises an annular recess 104 at its inside/lumen wall. This recess 104 allows for retaining cooperation with a corresponding and matching annular rib on a tracheostma device intended and adapted for cooperation with the tracheostoma device fitting 103.

Alternatively, the inside/lumen wall of the tracheostoma device fitting 103 may be provided with a rib, to correspond in a retaining manner with an annular recess on the tracheostoma device holder, in the same way.

The plate 101 is manufactured in a thermoplastic material, with a melting/softening temperature allowing for molding according to the local anatomic shape of the person through direct contact between the plate 101 and the skin of the person. Such thermoplastic may suitably be a polyester based thermoplastic, such as a polycaprolactone (PCL) based thermoplastic. Polycaprolactone is a biodegradable polyester with a low melting point of about 60° C. Once softened, it can be molded by hand in the proper shape. If the temperature of an outer layer decreases, it becomes non-sticky, but still pliable and moldable.

The plate 101 may be coated with acrylate, urethane, or a combination thereof, on its proximal side. This allows for easier handling during molding, since it decreases the stickiness to skin.

When adapting the tracheostoma device holder 100 in correspondence with the anatomy of the neck portion in the vicinity of the tracheostoma of the person intended to use the tracheostoma device holder 100, at least the plate 101 is heated to somewhat over the melting temperature of its thermoplastic material, i.e. approximately 65° C. in case of a PCL based thermoplastic. Normally, this is accomplished after approximately minutes of heating the plate 101 in warm water.

Figure 2:
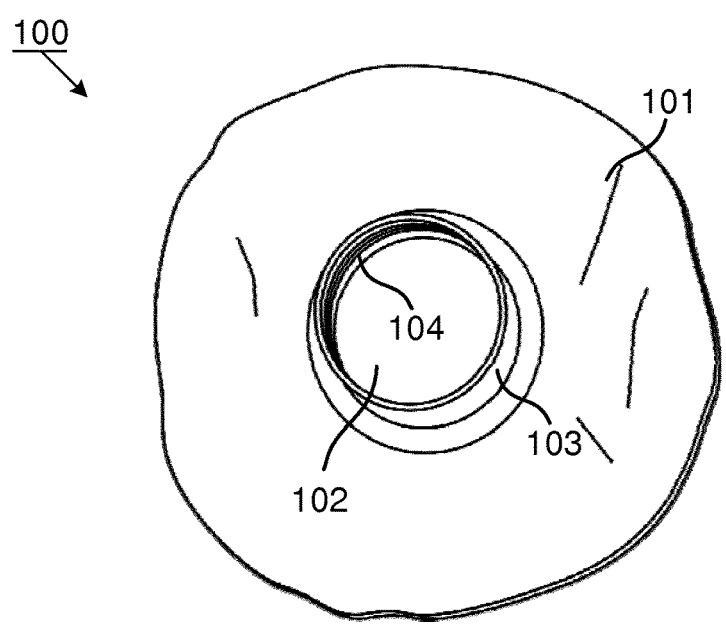
FIG. 2 is a perspective view of a tracheostoma device holder according to an embodiment of the present invention, in a post-adapted form.

After the plate 101 has reached its melting temperature, the plate 101 becomes compliable, and thus hand moldable. Also, when the thermoplastic material used is a PCL based thermoplastic, the plate changes in transparency from opaque to transparent. In this state, the plate is molded/shaped in accordance with the neck anatomy of the person, in accordance with FIG. 2, such that the through hole 102 is superimposed over the tracheostoma, such as for example disclosed in FIG. 3. The available molding time is normally about 2 minutes, whereafter the plate 101 turns unmoldable but still flexible. After approximately 30 minutes, the plate 101 again turns rigid, and is then ready for use. In this way, the plate may be molded in correspondence with the anatomy of the neck of the user, such that it conforms with for example the two vertical sternocleidomastoid muscles, as disclosed in FIG. 3, and still getting close also to sunken stomas. During speech, the pressure exerted from exhalation will be taken up by the entire plate 101, and the reluctance of the plate 101 to yield severely decreases the risk of flipping the tracheostoma device holder. Still further, due to the plate 101 being rigid in cured state, the entire plate 101 will have to move distally upon exerted pressure, which will decrease the risk of detachment at peripheral borders of the plate 101 against the skin of the person, which in turn improves the retaining properties of the plate 101. Additionally, due to the change in transparency at the melting temperature of PCL based materials, not only will it be easy to know when to start the molding process, but also it will be easy to adapt the plate 101 after the anatomy of the neck, since it will be possible to see through the plate 101 and detect and make up for contour changes at the neck. Also, the plate 101 may be simply remolded by reheating the plate 101 and reshaping it, if anatomy changes would occur or if it should be shaped in accordance with another user.

After cooling, i.e. after the plate 101 has returned into a rigid shape, the proximal side of the plate 101 may be provided with a tape or foam tape being adhesive on both sides, and at least skin adhesive on one of these. Such a tape may be dimensioned in accordance with the proximal side of the plate 101, such that the interaction surface between the plate 101 and the skin may be high. Alternatively, the plate 101 may be provided with a skin adhesive formulation on its proximal side through spraying or painting.

Figure 3:
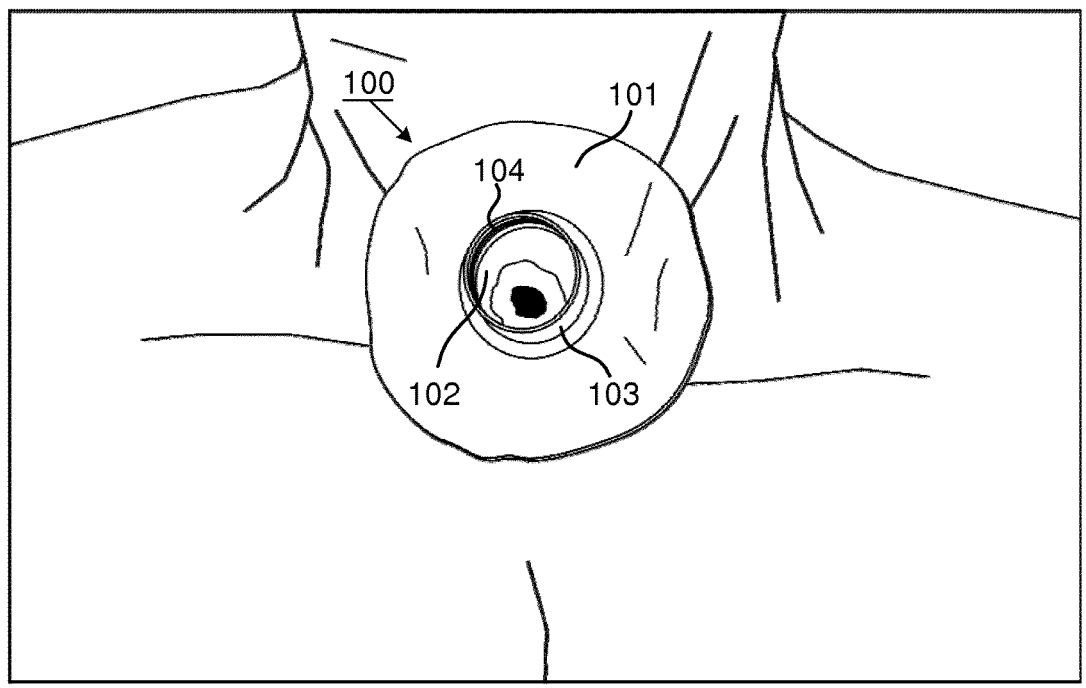
FIG. 3 is a perspective view of a tracheostoma device holder according to an embodiment of the present invention, in a post-adapted form placed on the neck of a person.

Thereafter, the plate 101 is attached to the neck of the user, such as disclosed in FIG. 3, such that the through hole 102 is superimposed over the tracheostoma, and a tracheostoma device, such as a speech valve, is connected to the trachestoma device fitting 103 in a known manner.

Since the plate 101 and the tracheostoma device fitting 103 are made of different materials, these parts may not be injection molded into a monolithic body. Instead, the plate 101 may be overmolded to the tracheostoma device fitting 103, or vice versa. The tracheostoma device fitting 103 may also be connected to the plate 101 through welding or gluing.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A tracheostoma device holder for holding a tracheostoma device superimposed on a tracheostoma of a person, the tracheostoma device holder comprising:
    a rigid plate for attachment over a tracheostoma via a proximal side thereof, the rigid plate including a through hole;
    a tubular tracheostoma device fitting, arranged circumferentially with the through hole, the tubular tracheostoma device fitting extending distally from a distal side of the rigid plate;
    wherein the rigid plate is comprised of a thermoplastic material having a melting/softening temperature configured to allow for molding of the rigid plate, after placing the rigid plate over the tracheostoma, according to the local anatomic shape of the person through close contact between the rigid plate and the skin of the person, wherein the rigid plate is flat before molding according to the local anatomic shape of the person.

2. The tracheostoma device holder according to claim 1, wherein the thermoplastic material is a polyester based thermoplastic.

3. The tracheostoma device holder according to claim 1, wherein the thermoplastic material is a polycaprolactone (PCL) based thermoplastic.

4. The tracheostoma device holder according to claim 1, wherein at least the proximal side of the rigid plate is coated with one or more of acrylate and urethane.

5. The tracheostoma device holder according to claim 1, wherein the tubular tracheostoma device fitting is a cylindrical sleeve.

6. The tracheostoma device holder according to claim 1, wherein the tubular tracheostoma device fitting includes an inside/lumen wall having at least one of an annular recess and rib formed therein.

7. The tracheostoma device holder according to claim 1, wherein the tubular tracheostoma device fitting at least partly is made of a flexible and resilient material.

8. The tracheostoma device holder according to claim 7, wherein the flexible and resilient material is comprised of one or more of a soft polyethylene, a polyethylene copolymer, a rubber and silicone.

9. The tracheostoma device holder according to claim 1, wherein the rigid plate and the tubular tracheostoma device fitting are brought into connection by overmolding.

10. The tracheostoma device holder according to claim 1, wherein at least the proximal side of the rigid plate includes a skin adhesive.

11. The tracheostoma device holder according to claim 10, wherein the skin adhesive is one of a tape, a foam tape, a sprayed skin adhesive, and a painted skin adhesive formulation;
    wherein the skin adhesive comprises a double sided adhesive and wherein the proximal side of the rigid plate is skin adhesive.

12. A method for adapting a tracheostoma device holder to neck anatomy of a person, comprising:
    heating a rigid plate including a thermoplastic material over a melting temperature of the thermoplastic material, such that the rigid plate becomes compliable and hand moldable;
    applying a proximal side of the rigid plate onto the neck of the person while the rigid plate is flat, such that a through hole formed in the rigid plate is superimposed over a tracheostoma of the person;
    shaping the rigid plate, after the applying of the rigid plate onto the neck, in accordance with the neck anatomy of the person; and
    actively or passively cooling the rigid plate below the melting temperature of the thermoplastic material.

13. The method according to claim 12, wherein the heating comprises temperatures over 60° C., and the cooling comprises temperatures below 60° C.

14. The method according to claim 12, further comprising; applying a skin adhesive surface on the proximal side of the rigid plate.

15. The method according to claim 14, wherein the skin adhesive surface is applied on the proximal side of the rigid plate through one of spraying a skin adhesive substance onto the proximal side, painting a skin adhesive substance onto the proximal side, applying a skin adhesive tape onto the proximal side, and foam tape onto the proximal side.

* * * * *